United States Patent
Katsumoto et al.

(10) Patent No.: US 9,388,313 B2
(45) Date of Patent: Jul. 12, 2016

(54) WATER-INSOLUBLE COLORING COMPOUND, INK, THERMAL TRANSFER RECORDING SHEET, AND COLOR FILTER RESIST COMPOSITION

(71) Applicant: CANON KABUSHIKI KAISHA, Tokyo (JP)

(72) Inventors: Yuko Katsumoto, Yokohama (JP); Shosei Mori, Hiratsuka (JP); Takeshi Sekiguchi, Tokyo (JP); Taichi Shintou, Saitama (JP); Takayuki Ujifusa, Ashigarakami-gun (JP); Takeshi Miyazaki, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/373,016

(22) PCT Filed: Jan. 16, 2013

(86) PCT No.: PCT/JP2013/051226
§ 371 (c)(1),
(2) Date: Jul. 17, 2014

(87) PCT Pub. No.: WO2013/108923
PCT Pub. Date: Jul. 25, 2013

(65) Prior Publication Data
US 2014/0349036 A1 Nov. 27, 2014

(30) Foreign Application Priority Data
Jan. 20, 2012 (JP) ................................ 2012-010326

(51) Int. Cl.
| | |
|---|---|
| *C09D 11/037* | (2014.01) |
| *C09D 11/322* | (2014.01) |
| *C09B 29/42* | (2006.01) |
| *C07D 213/80* | (2006.01) |
| *C07D 213/82* | (2006.01) |
| *B41M 5/388* | (2006.01) |
| *G02B 5/22* | (2006.01) |
| *G03F 7/00* | (2006.01) |
| *C09B 29/01* | (2006.01) |
| *C09D 11/00* | (2014.01) |

(52) U.S. Cl.
CPC ............ *C09B 29/0003* (2013.01); *B41M 5/388* (2013.01); *C07D 213/80* (2013.01); *C07D 213/82* (2013.01); *C09B 29/0007* (2013.01); *C09B 29/363* (2013.01); *C09D 11/00* (2013.01); *C09D 11/037* (2013.01); *C09D 11/322* (2013.01); *G02B 5/223* (2013.01); *G03F 7/0007* (2013.01)

(58) Field of Classification Search
CPC .. C09D 11/037; C09D 11/322; C09B 29/003; C09B 29/007; C09B 29/363; C07D 213/80; C07D 213/82; B41M 5/388; G02B 5/223; G03F 7/0007
USPC .................. 106/31.48; 534/772; 428/32.6
See application file for complete search history.

(56) References Cited

U.S. PATENT DOCUMENTS

| | | | | |
|---|---|---|---|---|
| 4,140,684 | A * | 2/1979 | Burkhard | C07D 213/80 534/772 |
| 7,193,068 | B2 * | 3/2007 | Araki | C07D 213/85 534/772 |
| 7,504,488 | B2 * | 3/2009 | Toyoda | C09B 29/0007 106/31.48 |
| 7,833,685 | B2 * | 11/2010 | Tanaka | C09B 29/0003 534/772 |
| 8,211,221 | B2 * | 7/2012 | Tanaka | C09D 11/328 106/31.48 |
| 8,211,606 | B2 * | 7/2012 | Murai | B41M 5/388 106/31.47 |
| 2009/0075193 | A1 * | 3/2009 | Murai | B41M 5/388 534/772 |
| 2010/0035171 | A1 * | 2/2010 | Watanabe | C09B 29/363 430/108.23 |
| 2014/0170553 | A1 * | 6/2014 | Mori | G03G 9/122 430/108.23 |
| 2015/0010865 | A1 * | 1/2015 | Mori | G03F 7/0007 430/281.1 |
| 2015/0140487 | A1 * | 5/2015 | Sekiguchi | G03G 9/0806 430/108.23 |

FOREIGN PATENT DOCUMENTS

| | | |
|---|---|---|
| DE | 2002022 A1 | 7/1971 |
| GB | 1360749 * | 7/1974 |
| JP | 2000-062327 A | 2/2000 |
| JP | 2006-124634 A | 5/2006 |
| WO | 2008/114886 A1 | 9/2008 |

OTHER PUBLICATIONS

Abstract of DE 2002022; Jul. 1971; 2 pages.*

* cited by examiner

*Primary Examiner* — Helene Klemanski
(74) *Attorney, Agent, or Firm* — Canon U.S.A., Inc., IP Division

(57) ABSTRACT

The present invention provides a water-insoluble coloring compound having a high solvent solubility, showing increased brightness and saturation, and being useful for increasing the green gamut and also provides an ink containing the water-insoluble coloring compound. The present invention provides a thermal transfer recording sheet including a coloring material layer formed on a base material from the ink and also provides a color filter resist composition showing an increased green gamut due to the ink.

8 Claims, 1 Drawing Sheet

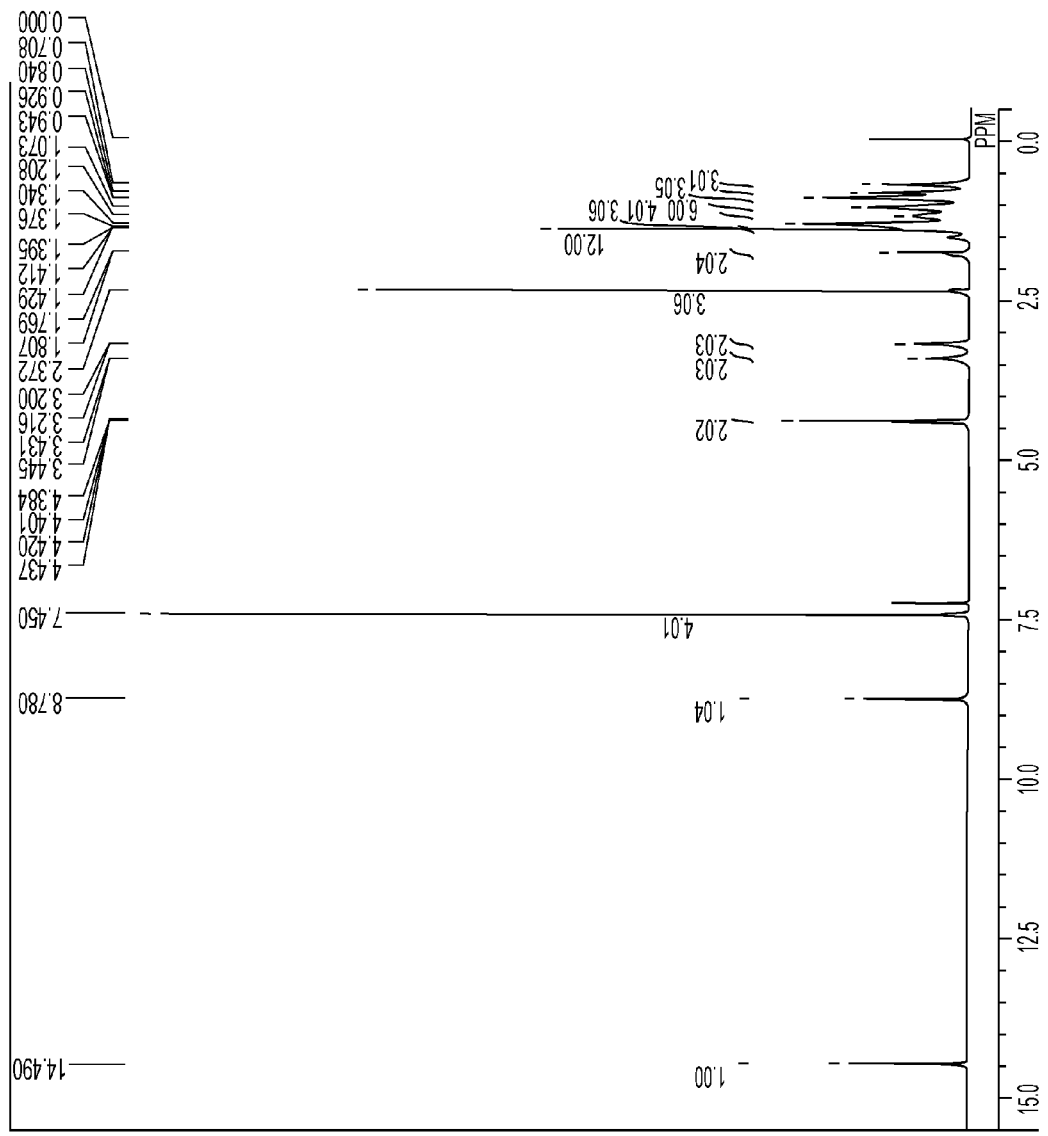

WATER-INSOLUBLE COLORING COMPOUND, INK, THERMAL TRANSFER RECORDING SHEET, AND COLOR FILTER RESIST COMPOSITION

TECHNICAL FIELD

The present invention relates to a water-insoluble coloring compound and relates to an ink, a thermal transfer recording sheet, and a color filter resist composition each containing the water-insoluble coloring compound.

BACKGROUND ART

Recently, higher image quality has been demanded in color images including color liquid crystal displays. A color filter is indispensable for color display of a liquid crystal display and is an important component that determines the performance of a display. Color filters can be produced by known methods such as a dyeing method, a printing method, an ink-jet method, and a photo-resist method. In particular, the photo-resist method can easily control the spectral characteristics and allows highly fine patterning because of its high resolution and is therefore a main method for producing color filters.

In the photo-resist method, the coloring agents are generally pigments. However, the pigment has a certain particle size and is thereby accompanied by a depolarization effect (i.e., collapse of polarization) to reduce the contrast ratio of color display of a liquid crystal display. Additionally, in a liquid crystal display using a pigment, since the pigment prevents the transmission of backlight, it is difficult to enhance the brightness of a color filter. Furthermore, the pigment is insoluble in organic solvents and polymers and therefore forms a dispersion in a color resist composition. Unfortunately, the stabilization of the dispersion is difficult.

In contrast, many dyes are generally soluble in organic solvents and polymers, and an appropriately selected dye can be stably present even in a color resist composition without aggregating. Accordingly, in a color filter produced from a resist composition containing a dye as the coloring agent, the dye is dispersed in a molecular level. As a result, the depolarization effect hardly occurs, and high transmission of backlight is provided.

Until now, the use of a yellow color filter containing a monoazo dye as a coloring agent has been proposed for enabling an image to be displayed with satisfactory spectral characteristics and high contrast (see Patent Literature 1). However, in order to display a finer image, it is necessary to develop a color filter having better spectral characteristics and achieving a higher contrast ratio.

Furthermore, there are demands for improvement of coloring compounds in other fields than color filters.

One of such demands is an image-forming method employing thermal transfer recording. The thermal transfer recording forms an image by stacking a thermal transfer sheet having a coloring material layer containing a heat-transferable coloring material and an image-receiving sheet having a surface provided with a coloring material-receiving layer on a sheet-like base material and heating the thermal transfer sheet to transfer the coloring material in the thermal transfer sheet to the image-receiving sheet and thereby to perform the recording. In the thermal transfer recording, the coloring compounds contained in the transfer sheet and in the ink composition for the transfer sheet highly affect the transfer recording speed and the quality and storage stability of the recorded matter and are therefore very important materials.

As the dyes used in such thermal transfer recording, methine disperse dyes such as C.I. Disperse Yellow 201, disazo disperse dyes such as C.I. Disperse Orange 13, and pyridone azo dyes have been proposed (see Patent Literature 2). However, there is even now a demand for developing a coloring compound having further enhanced characteristics such as saturation, color tone (in particular, expansion of the green gamut), and solvent solubility.

CITATION LIST

Patent Literature

PTL 1 Japanese Patent Laid-Open No. 2006-124634
PTL 2 Japanese Patent Laid-Open No. 2000-062327

SUMMARY OF INVENTION

The present invention provides a water-insoluble coloring compound having a high solvent solubility, a good saturation, and a good color tone, in particular, a good color tone in the green gamut.

The present invention also provides an ink, a color filter resist composition, and a thermal transfer recording sheet each showing a good saturation and a good color tone, in particular, a good color tone in the green gamut.

Solution to Problem

The above-described problems are solved by using the following water-insoluble coloring compound.

The present invention relates to a water-insoluble coloring compound having a structure represented by Formula (1):

[Chem. 1]

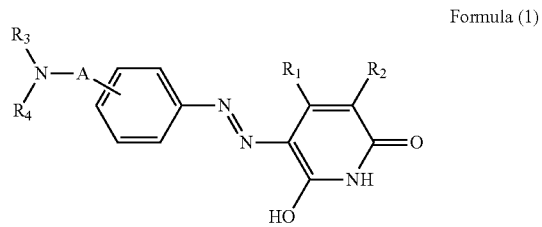

Formula (1)

(in Formula (1), $R_1$ represents an alkyl group, an aryl group, or an amino group; $R_2$ represents a carboxylic acid ester or a carboxylic acid amide; A represents a carbonyl group or a sulfonyl group; and $R_3$ and $R_4$ each independently represent an alkyl group or an aryl group).

The present invention also relates to an ink containing the water-insoluble coloring compound having a structure represented by Formula (1).

The present invention also relates to a thermal transfer recording sheet including a base material and a coloring material layer formed on the base material from a composition containing the water-insoluble coloring compound.

The present invention also relates to a color filter resist composition containing the water-insoluble coloring compound.

Advantageous Effects of Invention

The present invention can provide a water-insoluble coloring compound having a high solvent solubility, a good saturation, and a good color tone, in particular, a good color tone in the green gamut. Furthermore, the present invention can provide an ink, a color filter resist composition, and a thermal transfer recording sheet each showing a good saturation and a good color tone, in particular, a good color tone in the green gamut.

BRIEF DESCRIPTION OF DRAWINGS

FIG. 1 is a $^1$H-NMR spectrum of Compound (18), which is one of water-insoluble coloring compounds having a structure represented by Formula (1) of the present invention, in CDCl$_3$ at room temperature at 400 MHz.

DESCRIPTION OF EMBODIMENTS

The present invention will now be described in more detail.

The present inventors have diligently studied for solving the above-mentioned problems and, as a result, have found that the water-insoluble coloring compound having a structure represented by Formula (1) has a high solvent solubility, a good saturation, and a good color tone, in particular, a good color tone in the green gamut,

[Chem. 2]

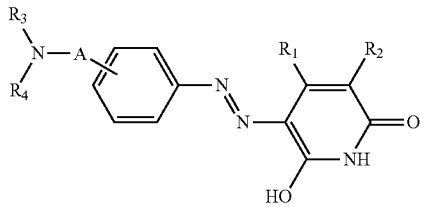

Formula (1)

(in Formula (1), $R_1$ represents an alkyl group, an aryl group, or an amino group; $R_2$ represents a carboxylic acid ester or a carboxylic acid amide; A represents a carbonyl group or a sulfonyl group; and $R_3$ and $R_4$ each independently represent an alkyl group or an aryl group).

The inventors have also found that an ink, a color filter resist composition, and a thermal transfer recording sheet each showing a good saturation and a good color tone, in particular, a good color tone in the green gamut can be provided by using the water-insoluble coloring compound and have accomplished the present invention.

The water-insoluble coloring compound having a structure represented by Formula (1) will now be described.

The water-insoluble coloring compound represented by Formula (1) of the present invention has high affinity to organic solvents. In the present invention, the term "water-insoluble" refers to that the solubility in water is less than 1% by mass.

In Formula (1), examples of the alkyl group represented by $R_1$ include, but are not limited to, a methyl group, an ethyl group, a propyl group, and a butyl group.

Examples of the aryl group represented by $R_1$ include, but are not limited to, a phenyl group.

Examples of the amino group represented by $R_1$ include, but are not limited to, an amino group, a propylamino group, a phenylamino group, a dimethylamino group, and a dipropylamino group.

$R_1$ can be an alkyl group. In particular, when $R_1$ is a methyl group, the color tone in the green gamut can be further enhanced.

In Formula (1), examples of the carboxylic acid ester represented by $R_2$ include, but are not limited to, a carboxylic acid methyl ester group, a carboxylic acid ethyl ester group, a carboxylic acid propyl ester group, a carboxylic acid butyl ester group, and a carboxylic acid 2-ethylhexyl ester group.

Examples of the carboxylic acid amide represented by $R_2$ include, but are not limited to, carboxylic acid dialkylamide groups such as a carboxylic acid dimethyl amide group and a carboxylic acid diethylamide group; carboxylic acid diphenylamide groups such as carboxylic acid diphenylamide group; carboxylic acid monoalkylamide groups such as a carboxylic acid methylamide group, a carboxylic acid ethylamide group, and a carboxylic acid t-butylamide group; and carboxylic acid monophenylamide groups such as carboxylic acid phenylamide group.

$R_2$ can be a carboxylic acid ester. In particular, a carboxylic acid methyl ester group and a carboxylic acid ethyl ester group increase the solvent solubility and provide good saturation and color tone and are particularly useful for providing a good color tone in the green gamut.

In Formula (1), examples of the alkyl group represented by $R_3$ or $R_4$ include, but are not limited to, saturated or unsaturated, linear, branched, or cyclic, and primary, secondary, or tertiary C1-20 alkyl groups such as a methyl group, an ethyl group, a n-propyl group, an iso-propyl group, a n-butyl group, a sec-butyl group, a tert-butyl group, an octyl group, a dodecyl group, a nonadecyl group, a cyclobutyl group, a cyclopentyl group, a cyclohexyl group, a methyl cyclohexyl group, a 2-ethylpropyl group, a 2-ethylhexyl group, and a cyclohexenyl ethyl group.

In Formula (1), examples of the aryl group represented by $R_3$ or $R_4$ include, but are not limited to, a phenyl group.

Among these groups, $R_3$ and $R_4$ can be each independently an ethyl group, a n-butyl group, a sec-butyl group, a dodecyl group, a cyclohexyl group, a methyl cyclohexyl group, a 2-ethylpropyl group, a 2-ethylhexyl group, or a cyclohexenyl ethyl group, in particular, a n-butyl group or a 2-ethylhexyl group, for increasing the solubility in solvents and providing a good color tone in the green gamut. Furthermore, $R_3$ and $R_4$ can be the same functional group, such as an alkyl group, for increasing the solubility in solvents.

The water-insoluble coloring compound having a structure represented by Formula (1) according to the present invention can be synthesized in accordance with the known method described in WO08/114,886.

An embodiment of the method of producing the water-insoluble coloring compound having a structure represented by Formula (1) of the present invention is shown below, but the method is not limited thereto.

[Chem. 3]

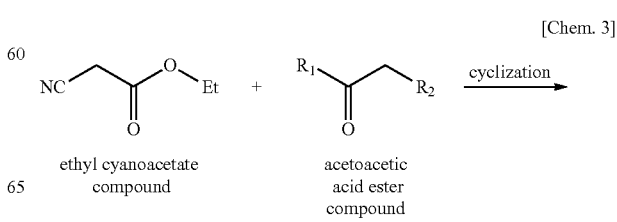

ethyl cyanoacetate compound     acetoacetic acid ester compound

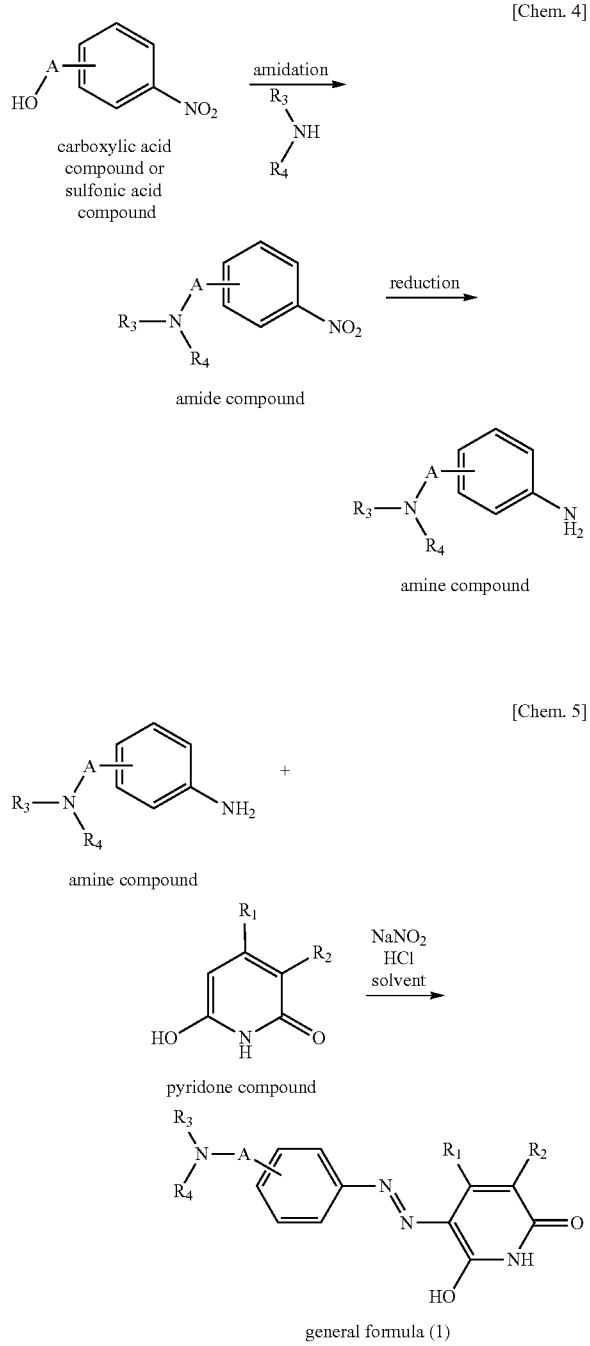

$R_1$ to $R_4$ and A in each compound in the reaction formulae and in general formula (1) are each independently synonymous with $R_1$ to $R_4$ and A in the above-mentioned Formula (1).

Incidentally, though Formula (1) shows an azo form, a tautomer of the structure represented by Formula (1), the hydrazo form, may be present together with the azo form.

The water-insoluble coloring compound of the present invention can be produced by coupling of a pyridone compound and an amine compound.

A method of producing the pyridone compound will be described.

The pyridone compound can be produced by cyclization using an ethyl cyanoacetate compound and an acetoacetic acid ester compound.

The cyclization process may be performed in the absence of a solvent, but is particularly performed in the presence of a solvent. Any solvent that does not participate in the reaction can be used without limitation, and examples of the solvent include water, methanol, ethanol, propanol, butanol, acetic acid, and toluene. In addition, a mixture of two or more solvents can be used, and the mixing ratio of the solvents can be appropriately determined. The amount of the reaction solvent used can be 0.1 to 1000 times, such as 1.0 to 150 times, the mass of the ethyl cyanoacetate compound.

The cyclization is facilitated by the presence of an acid or a base.

Examples of the usable acid include organic acids such as hydrochloric acid, sulfuric acid, and phosphoric acid; organic acids such as p-toluenesulfonic acid, formic acid, acetic acid, propionic acid, and trifluoroacetic acid; strong acid ion-exchange resins such as Amberlite (Rohm and Haas Co.) and Amberlist (Rohm and Haas Co.); and inorganic acid salts such as ammonium formate and ammonium acetate. Among these acids, in particular, hydrochloric acid can be used. The amount of the acid used can be 0.1 to 20 times, such as 0.8 to 10 times, and even 0.9 to 2.0 times the mass of the ethyl cyanoacetate compound.

Examples of the usable base include organic bases such as pyridine, 2-methylpyridine, diethylamine, diisopropylamine, triethylamine, phenylethylamine, isopropylethylamine, methylaniline, 1,4-diazabicyclo[2.2.2]octane (DABCO), tetrabutylammonium hydroxide, 1,8-diazabicyclo[5.4.0]undecene (DBU), and potassium acetate; organic metals such as n-butyllithium and tert-butyl magnesium chloride; inorganic bases such as sodium borohydride, metallic sodium, potassium hydride, and calcium oxide; and metal alkoxides such as potassium tert-butoxide, sodium tert-butoxide, and sodium ethoxide. Among these bases, in particular, triethylamine or piperidine, further triethylamine, can be used. The amount of the base used can be 0.1 to 20 times, such as 0.8 to 10 times, and even 0.9 to 2.0 times the mass of the ethyl cyanoacetate compound.

After the completion of the reaction, purification such as distillation, recrystallization, or silica gel chromatography is performed to yield a desired pyridone compound.

A method of producing the amine compound will be described.

The amine compound can be synthesized by preparing an amide compound through amidation of the carboxylic acid compound or the sulfonic acid compound and reducing the amide compound.

The carboxylic acid compound or the sulfonic acid compound used in the present invention and the amine compound used in the amidation process are commercially available and are therefore easily available.

The amidation process will now be described.

The amidation process may be performed in the absence of a solvent, but is particularly performed in the presence of a solvent. Any solvent that does not participate in the reaction can be used without limitation, and examples of the solvent include chloroform, dichloromethane, N,N-dimethylformamide, toluene, xylene, tetrahydrofuran, dioxane, acetonitrile, and ethyl acetate. In addition, a mixture of two or more solvents can be used, and the mixing ratio of the solvents can be appropriately determined. The amount of the reaction solvent used can be 0.1 to 1000 times, such as 1.0 to 150 times, of the mass of the carboxylic acid compound or the sulfonic acid compound.

The reaction temperature of the amidation process can be in the range of −80° C. to 250° C., such as −20° C. to 150° C. The amidation reaction is usually completed within 24 hours.

The amidation is facilitated by the presence of a chlorinating agent such as thionyl chloride or oxalyl chloride. There are many commercially available chlorinating agents. Among such chlorinating agents, thionyl chloride is inexpensively available and is easy to handle. The amount of thionyl chloride used can be 0.1 to 10 times, such as 0.5 to 5.0 times, and even 0.8 to 2.0 times the mass of the carboxylic acid compound or the sulfonic acid compound.

Furthermore, the reaction can be facilitated by the presence of a catalyst such as diethylamine, pyridine, or dimethylaminopyridine.

After the completion of the reaction, purification such as distillation, recrystallization, or silica gel chromatography is performed to yield a desired amide compound.

The reduction process will now be described.

The reduction process may be performed in the absence of a solvent, but is particularly performed in the presence of a solvent. Any solvent that does not participate in the reaction can be used without limitation, and examples of the solvent include water, methanol, ethanol, tetrahydrofuran, N,N-dimethylformamide, dichloromethane, dioxane, ethyl acetate, toluene, and acetonitrile. In addition, a mixture of two or more solvents can be used, and the mixing ratio of the solvents can be appropriately determined. The amount of the reaction solvent used can be 0.1 to 1000 times, such as 1.0 to 150 times, the mass of the carboxylic acid compound or the sulfonic acid compound.

Furthermore, the reduction is facilitated by the presence of a catalyst such as palladium on carbon. Furthermore, a reducing agent such as hydrogen, ammonium formate, or hydrazine can be used.

The reduction process may be performed under an ordinary pressure or under increased pressure with an apparatus such as an autoclave.

After the completion of the reaction, purification such as distillation, recrystallization, or silica gel chromatography is performed to yield a desired amine compound.

A process of forming a coloring compound by coupling of the pyridone compound and the amine compound will now be described.

The coloring compound can be formed by a known method. That is, the water-insoluble coloring compound having a structure represented by Formula (1) of the present invention can be prepared by coupling of the pyridone compound and a diazo component derived from the amine compound.

A specific example of the coupling will now be described.

The amine compound is reacted with a nitrite such as sodium nitrite in a solvent in the presence of an inorganic acid such as hydrochloric acid or sulfuric acid to be converted into the corresponding diazonium salt. The diazonium salt is subjected to coupling with the pyridone compound to produce a water-insoluble coloring compound having a structure represented by Formula (1).

The resulting water-insoluble coloring compound having a structure represented by Formula (1) is subjected to after-treatment that is usually performed in organic synthesis and then to purification, such as liquid separation, recrystallization, reprecipitation, or column chromatography, to yield a highly purified water-insoluble coloring compound. The resulting water-insoluble coloring compound having a structure represented by Formula (1) can be identified using a $^1$H nuclear magnetic resonance ($^1$H-NMR) spectrometer and a matrix-assisted laser desorption-ionization mass spectrometer (MALDI-TOF-MS).

The water-insoluble coloring compounds having a structure represented by Formula (1) of the present invention may be used alone or in combination for controlling, for example, the color tone according to the purpose of the use. Furthermore, the water-insoluble coloring compound can be used in combination with one or more known pigments or dyes.

As nonlimiting examples of the water-insoluble coloring compound of the present invention, the following Compounds (1) to (28) are shown.

[Chem. 6]

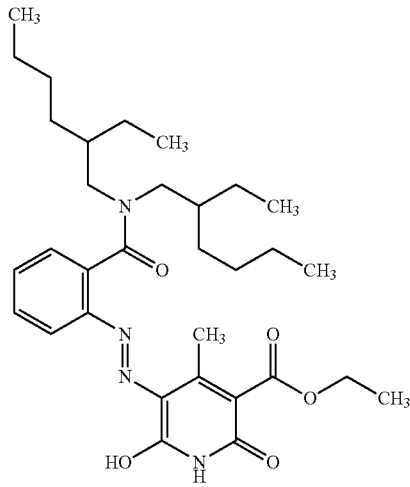

Compound (1)

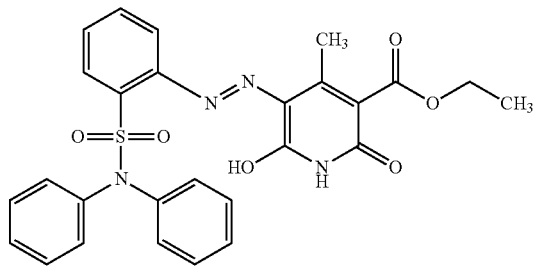

Compound (2)

-continued
Compound (3)
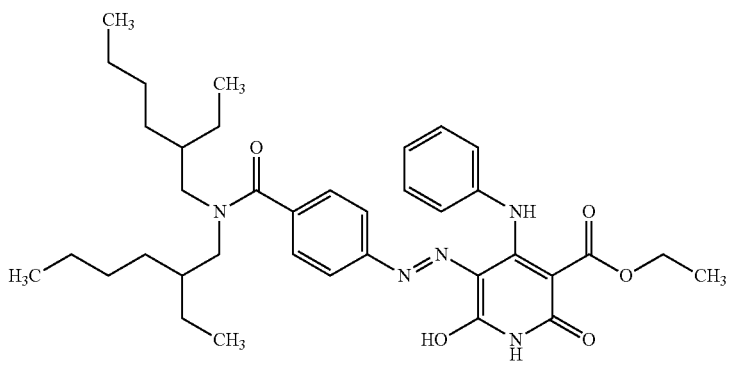
Compound (4)
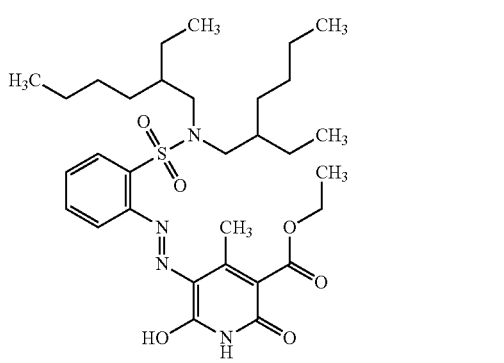
Compound (5)
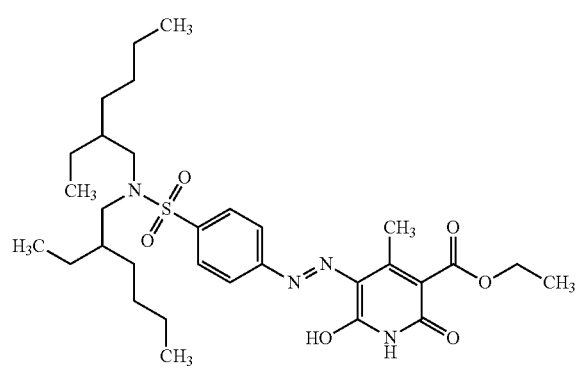
Compound (6)
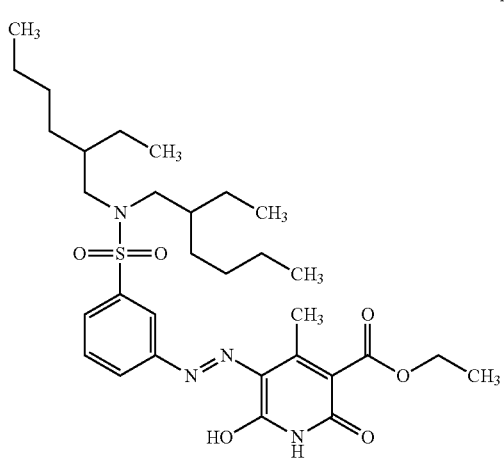
Compound (7)
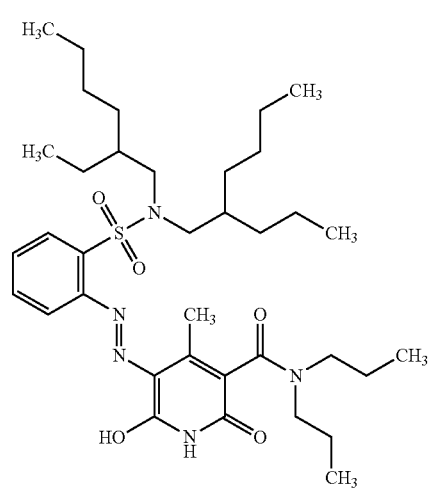
Compound (8)
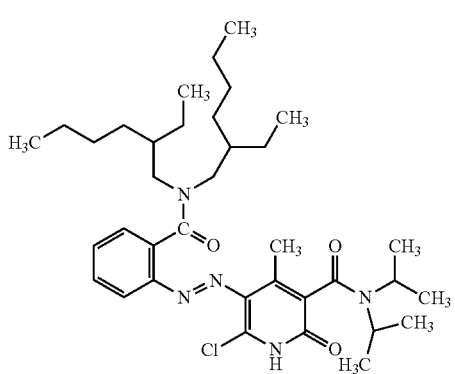

-continued
Compound (10)
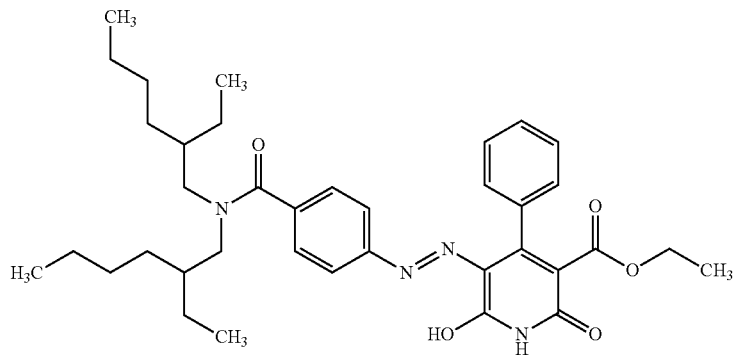
Compound (11)
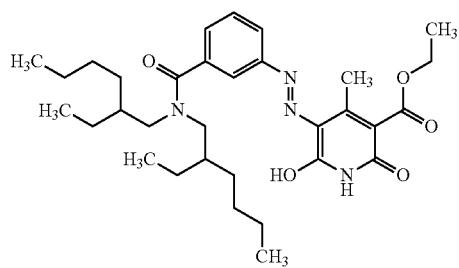
Compound (12)
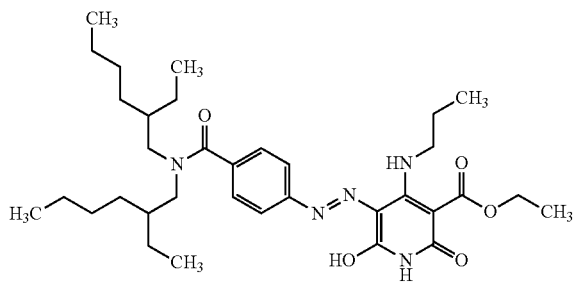
[Chem. 7]
Compound (13)
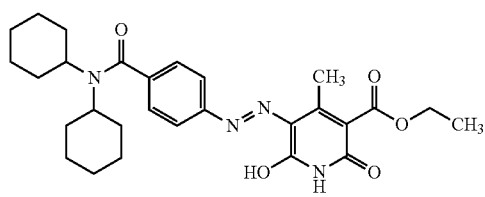
Compound (14)
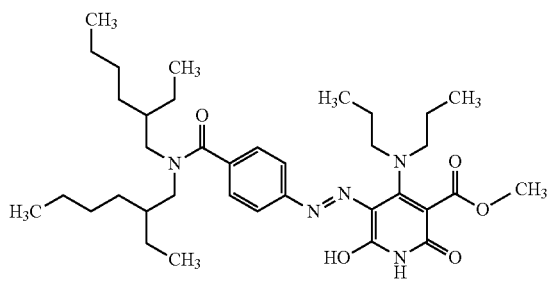
Compound (15)
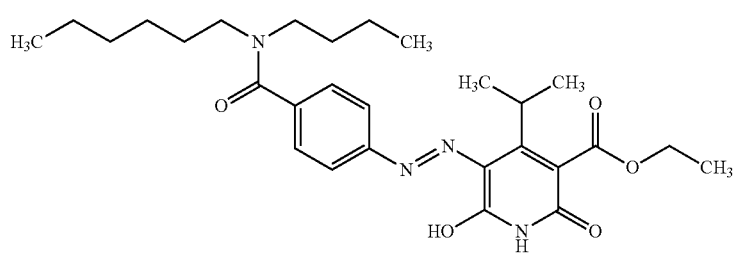

Compound (16)
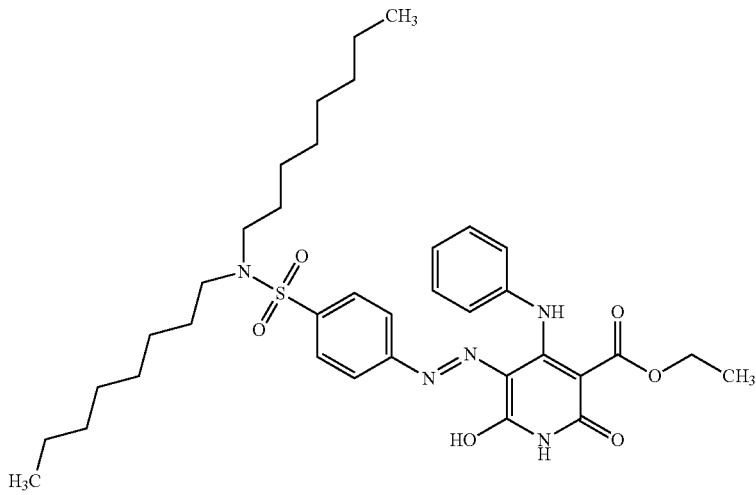
Compound (17)
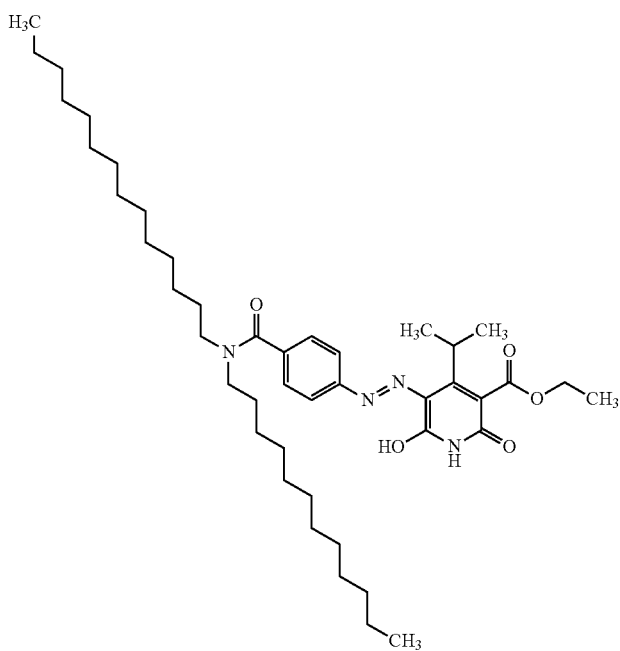
Compound (18)
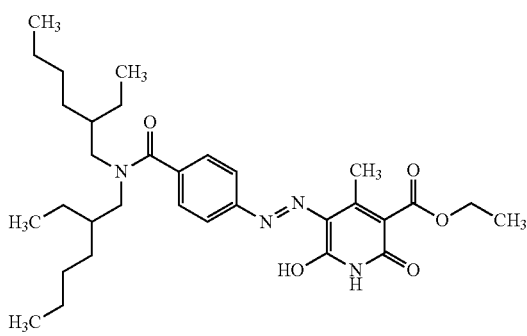
Compound (19)
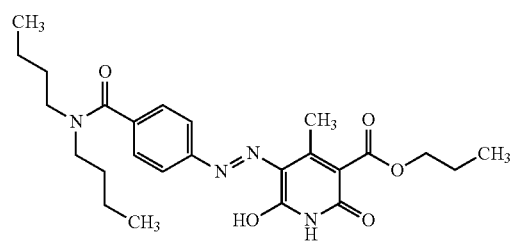

-continued
Compound (20)
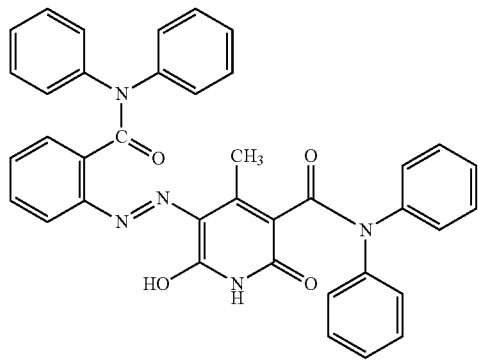
Compound (21)
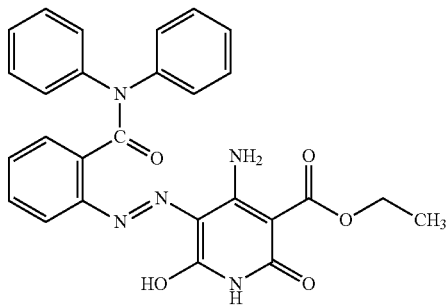
Compound (22)
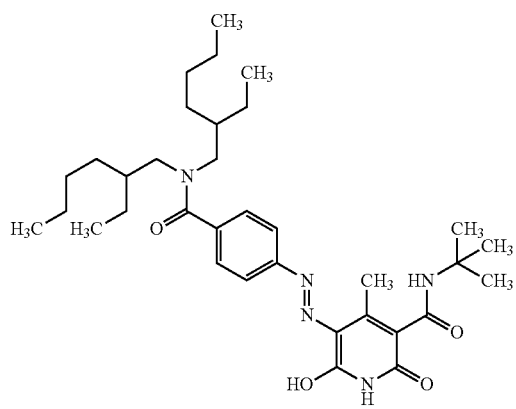
Compound (23)
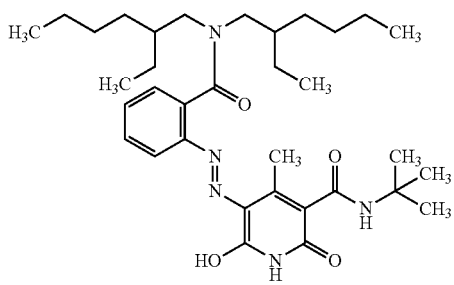
Compound (24)
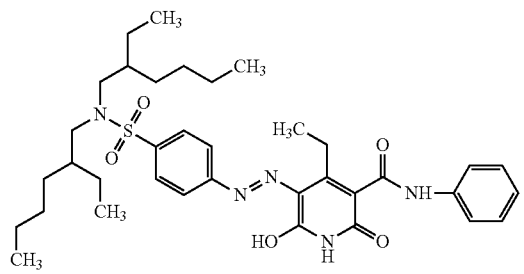
Compound (25)
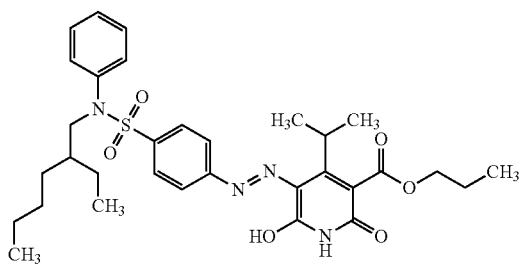
[Chem. 8]
Compound (26)
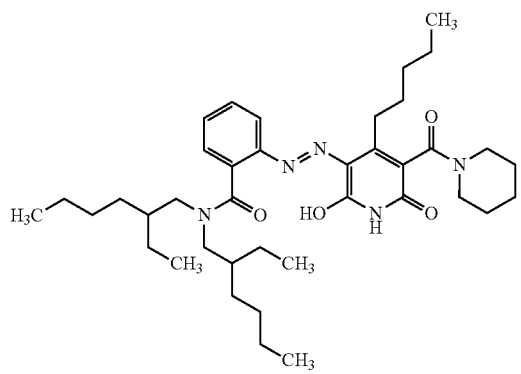
Compound (27)
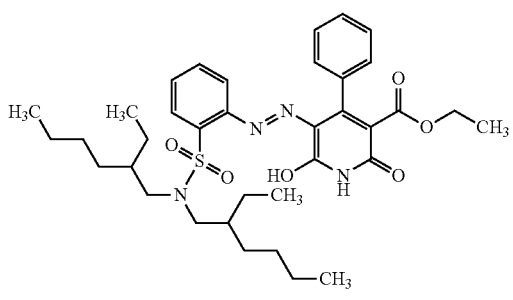

-continued

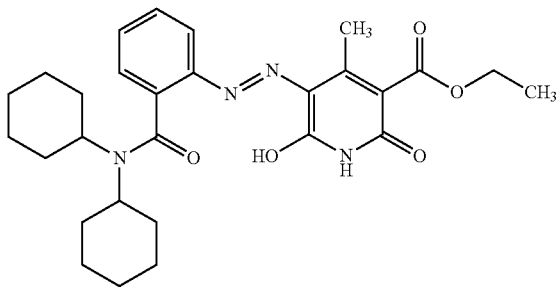

Compound (28)

Among Compounds (1) to (28), Compounds (1), (4), (10), (11), (18), (19), (20), (23), (24), (26), (27), and (28), in particular, Compounds (1), (4), (11), (18), (23), (26), and (28) are excellent.

Ink

The ink of the present invention will be described.

The water-insoluble coloring compound having a structure represented by Formula (1) of the present invention has a high solvent solubility, a good saturation, and a good color tone, in particular, a good color tone in the green gamut and therefore can be advantageously used as a coloring agent of an ink.

The ink of the present invention contains a medium and the water-insoluble coloring compound having a structure represented by Formula (1).

In the ink of the present invention, the structural components other than components described above can be determined depending on the use of the ink of the present invention. The ink may contain appropriate additives within the ranges that do not impair the characteristics of the ink in each use.

The ink of the present invention can be suitably used not only as an ink for ink jet printing but also as an ink for printing, painting, or writing. In particular, the ink can be suitably used as an ink for a color filter resist or as an ink for a thermal transfer recording sheet, described below.

The ink of the present invention can be prepared as follows.

A water-insoluble coloring compound of the present invention and optional another coloring agent, an emulsifier, and a resin are gradually added to a medium with stirring for mixing these components with the medium thoroughly and evenly. Furthermore, a mechanical shear force is applied to the mixture with a dispersing machine to allow the components to be dissolved or finely dispersed in the medium in a stable state to give an ink of the present invention.

In the present invention, the term "medium" refers to water or an organic solvent.

In the case of using an organic solvent as the medium of the ink of the present invention, the type of the organic solvent is determined depending on the intended use of the coloring agent and is not particularly limited. Examples of the organic solvent include alcohols such as methanol, ethanol, denatured ethanol, isopropanol, n-butanol, isobutanol, tert-butanol, sec-butanol, 2-methyl-2-butanol, 3-pentanol, octanol, benzyl alcohol, and cyclohexanol; glycols such as methyl cellosolve, ethyl cellosolve, diethylene glycol, and diethylene glycol monobutyl ether; ketones such as acetone, methyl ethyl ketone, and methyl isobutyl ketone; esters such as ethyl acetate, butyl acetate, ethyl propionate, and cellosolve acetate; aliphatic hydrocarbons such as hexane, octane, petroleum ether, and cyclohexane; aromatic hydrocarbons such as benzene, toluene, and xylene; halogenated hydrocarbons such as carbon tetrachloride, trichloroethylene, and tetrabromoethane; ethers such as diethyl ether, dimethyl glycol, trioxane, and tetrahydrofuran; acetals such as methylal and diethyl acetal; organic acids such as formic acid, acetic acid, and propionic acid; and sulfur- or nitrogen-containing organic compounds such as nitrobenzene, dimethylamine, monoethanolamine, pyridine, dimethyl sulfoxide, and dimethylformamide.

The organic solvent that can be used in the ink of the present invention may be a polymerizable monomer. The polymerizable monomer is an addition polymerizable or condensation polymerizable monomer and, in particular, can be an addition polymerizable monomer. Examples of the polymerizable monomer include styrene monomers such as styrene, α-methyl styrene, α-ethylstyrene, o-methylstyrene, m-methylstyrene, p-methylstyrene, o-ethylstyrene, m-ethylstyrene, and p-ethylstyrene; acrylate monomers such as methyl acrylate, ethyl acrylate, propyl acrylate, butyl acrylate, octyl acrylate, dodecyl acrylate, stearyl acrylate, behenyl acrylate, 2-ethylhexyl acrylate, dimethylaminoethyl acrylate, diethylaminoethyl acrylate, acrylonitrile, and amide acrylate; methacrylate monomers such as methyl methacrylate, ethyl methacrylate, propyl methacrylate, butyl methacrylate, octyl methacrylate, dodecyl methacrylate, stearyl methacrylate, behenyl methacrylate, 2-ethylhexyl methacrylate, dimethylaminoethyl methacrylate, diethylaminoethyl methacrylate, methacrylonitrile, and amide methacrylate; olefin monomers such as ethylene, propylene, butylene, butadiene, isoprene, isobutylene, and cyclohexene; halogenated vinyl monomers such as vinyl chloride, vinylidene chloride, vinyl bromide, and vinyl iodide; vinyl ester monomers such as vinyl acetate, vinyl propionate, and vinyl benzoate; vinyl ether monomers such as vinyl methyl ether, vinyl ethyl ether, and vinyl isobutyl ether; and vinyl ketone monomers such as vinyl methyl ketone, vinyl hexyl ketone, and methyl isopropenyl ketone. These monomers may be used alone or optionally in combination of two or more thereof.

As the coloring agent constituting the ink of the present invention, the water-insoluble coloring compound having a structure represented by Formula (1) is used. The ink can optionally contain another coloring agent that does not impair the solubility or dispersibility of the water-insoluble coloring compound in the medium.

Examples of the optional coloring agent that can be contained in the ink include, but are not limited to, C.I. Solvent Yellow 1, 19, 44, 49, 62, 74, 77, 79, 81, 82, 83, 89, 90, 93, 98, 103, 104, 112, 120, 121, 151, 153, 154, and 162; C.I. Pigment Yellow 1, 2, 3, 4, 5, 6, 7, 10, 11, 12, 13, 14, 15, 17, 23, 62, 65, 73, 74, 81, 83, 93, 94, 95, 97, 98, 109, 110, 111, 117, 120, 127, 128, 129, 137, 138, 139, 147, 150, 151, 154, 155, 167, 168, 173, 174, 176, 180, 181, 183, and 191; and various coloring agents classified as derivatives thereof.

The content of the coloring agent contained in the ink of the present invention can be 1.0 to 30.0 parts by mass, such as 2.0 to 20.0 parts by mass, and even 3.0 to 15.0 parts by mass, based on 100.0 parts by mass of the medium. In such a range, sufficient tinting strength is provided, and also satisfactory dispersibility of the coloring agent is achieved.

In the case of using water as the medium of the ink of the present invention, the ink can optionally contain an emulsifier for achieving satisfactory dispersion stability of the coloring agent. Examples of the usable emulsifier include, but are not limited to, cationic surfactants, anionic surfactants, and nonionic surfactants.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soaps such as sodium stearate and sodium dodecanoate; sodium dodecyl sulfate; sodium dodecyl benzene sulfate; and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

The ink of the present invention may further contain a resin. The type of the resin that can be contained in the ink of the present invention is determined depending on the intended use and is not particularly limited. Examples of the resin include polystyrene resins, styrene copolymers, polyacrylic acid resins, polymethacrylic acid resins, polyacrylic resins, polymethacrylic resins, acrylic acid copolymers, methacrylic acid copolymers, polyester resins, polyvinyl ether resins, polyvinyl methyl ether resins, polyvinyl alcohol resins, polyvinyl butyral resins, polyurethane resins, and polypeptide resins. These resins may be used alone or optionally in combination of two or more thereof.

Any dispersing machine can be used in production of the ink without limitation. For example, a rotation shearing-type homogenizer, a media type dispersing machine such as a ball mill, a sand mill, or an attritor, or a high-pressure countercollision type dispersing machine can be used.

As described above, the ink of the present invention contains the water-insoluble coloring compound of the present invention and thereby has a good saturation and a good color tone, in particular, a good color tone in the green gamut.

Thermal Transfer Recording Sheet

The thermal transfer recording sheet of the present invention will now be described.

The water-insoluble coloring compound of the present invention has a high solvent solubility, a good saturation, and a good color tone, in particular, a good color tone in the green gamut and therefore can be suitably applied to a thermal transfer recording sheet.

The thermal transfer recording sheet of the present invention includes a base material and a coloring material layer formed on the base material from a composition containing the water-insoluble coloring compound of the present invention.

The thermal transfer recording sheet of the present invention can be prepared as follows. A coloring agent containing the water-insoluble coloring compound having a structure represented by Formula (1) and a binder resin and optionally a surfactant and a wax are gradually added to a medium with stirring for mixing these components with the medium thoroughly and evenly. Furthermore, a mechanical shear force is applied to the mixture with a dispersing machine to allow the components to be dissolved or finely dispersed in the medium in a stable state to prepare the ink of the present invention. Subsequently, the ink is applied to a base film as the base material and dried to produce a thermal transfer recording sheet of the present invention, but the present invention is not limited to the thermal transfer recording sheet produced by this process as long as the thermal transfer recording sheet includes the water-insoluble coloring compound having a structure represented by Formula (1).

Various resins can be used as the binder resin for the coloring material layer of the thermal transfer recording sheet of the present invention. Specific examples thereof include water-soluble resins such as cellulose resins, polyacrylic acid resins, starch resins, and epoxy resins; and organic solvent-soluble resins such as polyacrylic resins, polymethacrylic resins, polystyrene resins, polycarbonate resins, polyether sulfone resins, polyvinyl butyral resins, ethyl cellulose resins, acetyl cellulose resins, polyester resins, AS resins, and phenoxy resins. These resins may be used alone or optionally in combination of two or more thereof.

The medium used in the method of producing the thermal transfer recording sheet may be the same as those that are used as the medium of the ink. Specific examples of the medium include water and organic solvents. Examples of the organic solvent include alcohols such as methanol, ethanol, isopropanol, and isobutanol; cellosolves such as methyl cellosolve and ethyl cellosolve; aromatic hydrocarbons such as toluene, xylene, and chlorobenzene; esters such as ethyl acetate and butyl acetate; ketones such as acetone, methyl ethyl ketone, methyl isobutyl ketone, and cyclohexanone; halogenated hydrocarbons such as methylene chloride, chloroform, and trichloroethylene; ethers such as tetrahydrofuran and dioxane; N,N-dimethylformamide; and N-methylpyrrolidone. The organic solvents may be used alone or optionally in combination of two or more thereof.

The thermal transfer recording sheet of the present invention contains the water-insoluble coloring compound having a structure represented by Formula (1) as the coloring agent and thereby has a good color tone in the green gamut. Furthermore, the thermal transfer recording sheet may contain another coloring agent for toning in order to provide desired spectral characteristics. Any optional coloring agent that does not highly affect the saturation and the color tone (in particular, the color tone in the green gamut) of the thermal transfer recording sheet of the present invention can be used without limitation. Examples of the optional coloring agent include, but are not limited to, C.I. Solvent Yellow 1, 19, 44, 49, 62, 74, 77, 79, 81, 82, 83, 89, 90, 93, 98, 103, 104, 112, 120, 121, 151, 153, 154, and 162; and various coloring agents classified as derivatives thereof.

The mass ratio of the binder resin to the coloring agent (the use ratio of (binder resin):(coloring agent)) can be in a range of 1:2 to 2:1, from the viewpoint of a transferring property.

The thermal transfer recording sheet of the present invention may contain a surfactant for having a sufficient lubricating property during heating the thermal head (during printing). Examples of the surfactant that can be contained in the thermal transfer recording sheet include cationic surfactants, anionic surfactants, and nonionic surfactants.

Examples of the cationic surfactant include dodecyl ammonium chloride, dodecyl ammonium bromide, dodecyl trimethyl ammonium bromide, dodecyl pyridinium chloride, dodecyl pyridinium bromide, and hexadecyl trimethyl ammonium bromide.

Examples of the anionic surfactant include fatty acid soaps such as sodium stearate and sodium dodecanoate; sodium dodecyl sulfate; sodium dodecyl benzene sulfate; and sodium lauryl sulfate.

Examples of the nonionic surfactant include dodecyl polyoxyethylene ether, hexadecyl polyoxyethylene ether, nonylphenyl polyoxyethylene ether, lauryl polyoxyethylene ether, sorbitan monooleate polyoxyethylene ether, and monodecanoyl sucrose.

The thermal transfer recording sheet of the present invention may contain a wax for having a sufficient lubricating property during non-heating the thermal head. Examples of the wax that can be contained in the thermal transfer recording sheet include, but are not limited to, polyethylene waxes, paraffin waxes, and fatty acid ester waxes.

The thermal transfer recording sheet of the present invention may optionally contain an ultraviolet absorber, an antiseptic, an antioxidant, an anti-static agent, or a viscosity modifier, in addition to the above-described additives.

Any base film can be used as the base material for the thermal transfer recording sheet of the present invention without limitation. For example, thin paper such as condenser paper or glassine paper or a plastic film of polyester, polycarbonate, polyamide, polyimide, or polyaramide can be used from the viewpoint of high heat resistance; and a polyethylene terephthalate film can be used from the viewpoints of mechanical strength, solvent resistance, and cost performance. The thickness of the base material can be 3 to 50 μm from the viewpoint of a transferring property.

The thermal transfer recording sheet of the present invention can have a layer of a lubricant, a heat-resistant fine particles having a high lubricating property, and a thermal resin such as a binding agent on the opposite side of the base material from the coloring material layer, for increasing the heat resistance and the mobility of the thermal head. Examples of the lubricant include, but are not limited to, amino-modified silicone compounds and carboxy-modified silicone compounds. Examples of the heat-resistant fine particles include, but are not limited to, fine particles such as silica, and examples of the binding agent include, but are not limited to, acrylic resins.

Any dispersing machine can be used in the dispersing step without limitation. For example, a rotation shearing-type homogenizer, a media type dispersing machine such as a ball mill, a sand mill, and an attritor, or a high-pressure counter-collision type dispersing machine can be used.

The ink composition may be applied to the base film by any method without limitation, for example, a method using a bar coater, a gravure coater, a reverse roll coater, a rod coater, or an air doctor coater. The application amount of the ink composition can be controlled so that the coloring material layer after drying has a thickness of 0.1 to 5 μm, from the viewpoint of a transferring property.

The thermal transfer recording sheet of the present invention may be heated by any method without limitation. For example, not only a thermal head, which is usually used, but also infrared rays or a laser can be used. Alternatively, an electrical conduction exothermic film that generates heat by electrifying the base film itself may be used as an electrical conduction-type dye transfer sheet.

As described above, the thermal transfer recording sheet of the present invention contains the ink of the present invention and thereby has a good saturation and a good color tone, in particular, a good color tone in the green gamut.

Color Filter Resist Composition

The color filter resist composition of the present invention will now be described.

The water-insoluble coloring compound of the present invention has a high solvent solubility, a good saturation, and a good color tone, in particular, a good color tone in the green gamut and therefore can be suitably applied to a color filter resist composition.

The color filter resist composition of the present invention contains a binder resin, a medium, and the water-insoluble coloring compound of the present invention.

The color filter resist composition of the present invention is prepared as follows. The water-insoluble coloring compound and a binder resin are added to a medium with stirring. The color filter resist composition may optionally contain a polymerizable monomer, a polymerization initiator, and a photoacid generator. Subsequently, a mechanical shear force is applied to the mixture with a dispersing machine to allow the components to be dissolved or finely dispersed in the medium in a stable state to give the color filter resist composition of the present invention.

Any binder resin can be used in the color filter resist composition of the present invention, as long as either a light-irradiating portion or a light-shielding portion in the exposure process of pixel formation is soluble in an organic solvent, an alkali aqueous solution, water, or a commercially available developing solution. In particular, a resin having a composition that allows developing in water or an alkali aqueous solution can be used from the viewpoints of workability and treatment after resist production.

The usable binder resin can be formed by copolymerizing a hydrophilic polymerizable monomer and a hydrophobic polymerizable monomer at an appropriate mixing ratio by a known method. Typical examples of the hydrophilic polymerizable monomer include acrylic acid, methacrylic acid, N-(2-hydroxyethyl)acrylamide, N-vinylpyrrolidone, and polymerizable monomers having ammonium salts. Typical examples of the hydrophobic polymerizable monomer include acrylic acid ester, methacrylic acid ester, vinyl acetate, styrene, and N-vinylcarbazole. Such a binder resin can be used as a negative-type resist, where the solubility of materials in a developing solution is decreased by exposure to light and thereby the exposure portion remains and only the light-shielding portion is removed by developing, in combination with a radical polymerizable monomer having an ethyleny unsaturated group, a cationic polymerizable monomer having an oxirane ring or an oxetane ring, a radical-generating agent, an acid-generating agent, and a base-generating agent.

A combination of a resin having a quinone diazide group that is cleaved by light and generates a carboxylic acid group; a binder resin having a group that is cleaved by an acid represented by tert-butylcarbonate of polyhydroxystyrene or tetrahydropyranyl ether; and an acid-generating agent that generates an acid by exposure to light can be used. Such a binder resin can be used as a positive resist, where the solubility of materials in a developing solution is increased by exposure to light and thereby the light-shielding portion remains and only the exposure portion is removed by developing.

When the color filter resist composition of the present invention is a negative-type resist composition, a polymerizable monomer that is addition-polymerized by exposure to light (hereinafter, also referred to as a photopolymerizable monomer) can be used. The photopolymerizable monomer can be a compound having at least one addition polymerizable ethyleny unsaturated double bond in the molecule and having a boiling point of 100° C. or more at ordinary pressure. Specific examples of the photopolymerizable monomer include monofunctional acrylates and methacrylates such as polyethylene glycol monoacrylate, polyethylene glycol monomethacrylate, polypropylene glycol monoacrylate, polypropylene glycol monomethacrylate, phenoxyethyl acrylate, and phenoxyethyl methacrylate; multi-functional acrylates and methacrylates such as polyethylene glycol diacrylate, polyethylene glycol dimethacrylate, polypropylene glycol diacrylate, polypropylene glycol dimethacrylate, trimethylol ethane triacrylate, trimethylol ethane trimethacrylate, trimethylol propane triacrylate, trimethylol propane trimethacrylate, trimethylol propane diacrylate, trimethylol propane dimethacrylate, neopentyl glycol diacrylate, neopentyl glycol dimethacrylate, pentaerythritol tetraacrylate, pentaerythritol tetramethacrylate, pentaerythritol triacrylate, pentaerythritol trimethacrylate, dipentaerythritol hexaacrylate, dipentaerythritol hexamethacrylate, dipentaerythritol pentaacrylate, dipentaerythritol pentamethacrylate, hexanediol diacrylate, hexanediol dimethacrylate, trimethylol propane tri(acryloyloxypropyl)ether, tri(acryloyloxyethyl) isocyanurate, tri(acryloyloxyethyl)cyanurate, glycerin triacrylate, and glycerin trimethacrylate; and multi-functional acrylates and methacrylates obtained by adding ethylene oxide or propylene oxide to a multi-functional alcohol such as trimethylol propane or glycerin and then subjecting the products to acrylation or methacrylation. Examples of the photopolymerizable monomer further include multi-functional epoxy acrylates and epoxy methacrylates, which are reaction products of acrylic acid or methacrylic acid with a urethane acrylate, a polyester acrylate, or an epoxy resin. In particular, trimethylol propane triacrylate, trimethylol propane trimethacrylate, pentaerythritol tetraacrylate, pentaerythritol tetramethacrylate, dipentaerythritol hexaacrylate, dipentaerythritol hexamethacrylate, dipentaerythritol pentaacrylate, and dipentaerythritol pentamethacrylate can be used.

The above-mentioned photopolymerizable monomers may be used alone or optionally in combination of two or more thereof.

The content of the photopolymerizable monomer may be 5 to 50% by mass, such as 10 to 40% by mass, based on the mass of the resist composition (the entire solid content excluding the solvent) of the present invention. A content of 5 to 50% by mass can further enhance the sensitivity to exposure and the strength of pixels and can allow the adhesiveness of the resist composition to be in an appropriate state.

When the color filter resist composition of the present invention is a negative-type, the composition may contain a photopolymerization initiator. Examples of the photopolymerization initiator include a vicinal polyketoaldonyl compounds, α-carbonyl compounds, asioin ethers, various quinone compounds, combinations of triallylimidazole dimers and p-aminophenylketone, and trioxadiazole compounds. In particular, 2-benzyl-2-dimethylamino-1-(4-morpholinophenyl)butanone (Trade name: Irgacure 369, manufactured by BASF AG) can be used. When electron rays are used in pixel formation with a color resist of the present invention, the photopolymerization initiator is not essential.

When the color filter resist composition of the present invention is a positive-type, the composition may optionally contain a photoacid generator. The photoacid generator may be a known one such as salts of anions and onium ions such as sulfonium, iodonium, selenium, ammonium, and phosphonium ions.

Examples of the sulfonium ion include triphenylsulfonium, tri-p-tolylsulfonium, tri-o-tolylsulfonium, tris(4-methoxyphenyl)sulfonium, 1-naphthyldiphenylsulfonium, diphenylphenacylsulfonium, phenylmethylbenzylsulfonium, 4-hydroxyphenylmethylbenzylsulfonium, dimethylphenacylsulfonium, and phenacyltetrahydrothiophenium.

Examples of the iodonium ion include diphenyliodonium, di-p-tolyliodonium, bis(4-dodecylphenyl)iodonium, bis(4-methoxyphenyl)iodonium, and (4-octyloxyphenyl)phenyliodonium.

Examples of the selenium ion include triarylseleniums such as triphenylselenium, tri-p-tolylselenium, tri-o-tolylselenium, tris(4-methoxyphenyl)selenium, 1-naphtyldiphenylselenium, tris(4-fluorophenyl)selenium, tri-1-naphthylselenium, and tri-2-naphthylselenium.

Examples of the ammonium ion include tetraalkylammoniums such as tetramethylammonium, ethyltrimethylammonium, diethyldimethylammonium, triethylmethylammonium, tetraethylammonium, trimethyl-n-propylammonium, trimethylisopropylammonium, trimethyl-n-butylammonium, and trimethylisobutylammonium.

Examples of the phosphonium ion include tetraphenylphosphonium, tetra-p-tolylphosphonium, tetrakis(2-methoxyphenyl)phosphonium, triphenylbenzylphosphonium, triphenylphenacylphosphonium, triphenylmethylphosphonium, triethylbenzylphosphonium, and tetraethylphosphonium.

Examples of the anion include, but are not limited to, perhalogenic acid ions such as $ClO_4^-$ and $BrO_4^-$; halogenated sulfonate ions such as $FSO_3^-$ and $ClSO_3^-$; sulfate ions such as $CH_3SO_4^-$, $CF_3SO_4^-$, and $HSO_4^-$; carbonate ions such as $HCO_3^-$ and $CH_3CO_3^-$; aluminate ions such as $AlCl_4^-$ and $AlF_4^-$; hexafluorobismuthic acid ions; carboxylate ions such as $CH_3COO^-$, $CF_3COO^-$, $C_6H_5COO^-$, $CH_3C_6H_4COO^-$, $C_6F_5COO^-$, and $CF_3C_6H_4COO^-$; arylborate ions such as $B(C_6H_5)_4^-$ and $CH_3CH_2CH_2CH_2B(C_6H_5)_3^-$; thiocyanate ions; and nitrate ions.

In the color filter resist composition of the present invention, water or an organic solvent is used as the medium for dissolving or dispersing the water-insoluble coloring compound, a binder resin, and optional photopolymerizable monomer, photopolymerization initiator, and photoacid generator. Examples of the organic solvent include cyclohexanone, ethyl cellosolve acetate, butyl cellosolve acetate, 1-methoxy-2-propyl acetate, diethylene glycol dimethyl ether, ethyl benzene, 1,2,4-trichlorobenzene, ethylene glycol diethyl ether, xylene, ethyl cellosolve, methyl-n-amyl ketone, propylene glycol monomethyl ether, toluene, methyl ethyl ketone, ethyl acetate, methanol, ethanol, isopropanol, butanol, methyl isobutyl ketone, and petroleum solvents. These organic solvents can be used alone or in combination of two or more thereof.

In a color filter where two or more pixels having different spectral characteristics are arranged so as to be adjacent to each other, the color filter can have a good saturation and a good color tone, in particular, a good color in the green gamut by using the resist composition of the present invention in the pixels constituting at least one color among the plurality of colors (e.g., red, green, and blue) of the pixels. In order to provide desired spectral characteristics, the composition may contain another dye for toning. Any dye can be used as the additional dye without limitation, and examples of the dye include C.I. Solvent Blue 14, 24, 25, 26, 34, 37, 38, 39, 42, 43, 44, 45, 48, 52, 53, 55, 59, 67, and 70; and C.I. Solvent Red 8, 27, 35, 36, 37, 38, 39, 40, 49, 58, 60, 65, 69, 81, 83:1, 86, 89, 91, 92, 97, 99, 100, 109, 118, 119, 122, 127, and 218.

The color filter resist composition of the present invention may contain an ultraviolet absorber and a silane coupling agent for enhancing the adhesiveness with a glass substrate in the process of producing the filter, as necessary, in addition to the above-described additives.

Any dispersing machine may be used for producing the resist solution containing the resist composition without limitation. For example, a rotation shearing-type homogenizer, a media type dispersing machine such as a ball mill, a sand mill, or an attritor, or a high-pressure counter-collision type dispersing machine can be used.

As described above, the color filter resist composition of the present invention contains the water-insoluble coloring compound of the present invention and thereby has a good saturation and a good color tone, in particular, a good color tone in the green gamut.

EXAMPLES

The present invention will be described in more detail by the following Examples and Comparative Examples, but is not limited to these Examples. Note that "part(s)" and "%" in Examples and Comparative Examples are based on mass unless otherwise specified. The prepared reaction products were identified using a $^1$H nuclear magnetic resonance ($^1$H NMR) spectrometer (ECA-400, manufactured by JEOL Ltd.) and a matrix-assisted laser desorption-ionization mass spectrometer (MALDI-TOF-MS) (autoflex apparatus, manufactured by Bruker Daltonics K.K.). In the MALDI-TOF-MS, the negative mode was employed for detecting ions.

Production of Water-Insoluble Coloring Compound Having a Structure Represented by Formula (1)

The water-insoluble coloring compound having a structure represented by Formula (1) of the present invention can be synthesized by a known process.

The water-insoluble coloring compounds having a structure represented by Formula (1) of the present invention were produced by the process described below. Furthermore, the solubilities of the resulting water-insoluble coloring compounds in water at room temperature and at 60° C. were measured and were confirmed to be less than 1% by mass.

Example 1

Production of Compound (1)

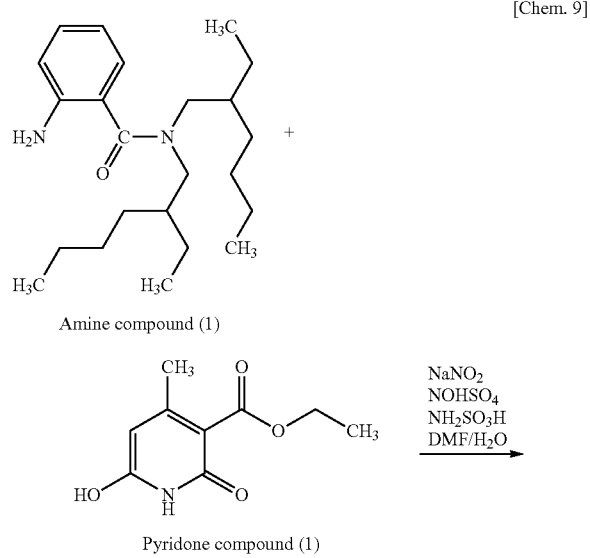

Amine compound (1)

NaNO$_2$
NOHSO$_4$
NH$_2$SO$_3$H
DMF/H$_2$O

Pyridone compound (1)

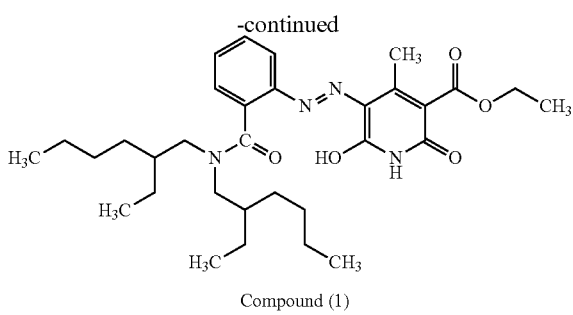

Compound (1)

A solution of 3.00 g of amine compound (1) in 20 mL of N,N-dimethylformamide was cooled to 5° C., and a solution of 4.05 g of 40% nitrosylsulfuric acid in 20 mL of N,N-dimethylformamide was slowly dropwise added thereto. Furthermore, a solution of 0.63 g of sodium nitrite in 3 mL of water was dropwise added thereto, followed by stirring for 1 hour. Furthermore, 0.13 g of amidosulfuric acid was added to the reaction solution to decompose excess nitrosylsulfuric acid to prepare diazotization solution A. Separately, a solution of 1.64 g of pyridone compound (1) in 8 mL of dimethylformamide was cooled to 5° C., and diazotization solution A was slowly dropwise added thereto while maintaining the temperature at 5° C. or less, followed by stirring at 0 to 5° C. for further 2 hours. After the completion of the reaction, extraction with chloroform was performed. The chloroform layer was concentrated, and the resulting solid was purified by column chromatography (eluent: heptane/chloroform) and was recrystallized from a heptane/chloroform solution to yield 3.55 g of Compound (1).

Analytical Results of Compound (1)

[1] $^1$H-NMR (400 MHz, CDCl$_3$, room temperature): δ (ppm)=0.59-0.67 (3H, m), 0.72-0.79 (3H, m), 0.88-1.16 (14H, m), 1.27-1.45 (11H, m), 1.68-1.89 (2H, m), 2.37 (3H, s), 3.24 (2H, d, J=6.10 Hz), 3.35-3.71 (2H, m), 4.41 (2H, q, J=7.12 Hz), 7.20 (1H, dd, J=7.63 Hz, 7.63 Hz), 7.26 (1H, d, J=7.63 Hz), 7.46 (1H, dd, J=7.63 Hz, 7.63 Hz), 7.84 (1H, d, J=7.63 Hz), 8.14 (1H, s), 14.74 (1H, s).

[2] Mass spectrometry by MALDI-TOF-MS: m/z=567.783 (M-H)$^-$

Example 2

Production of Compound (4)

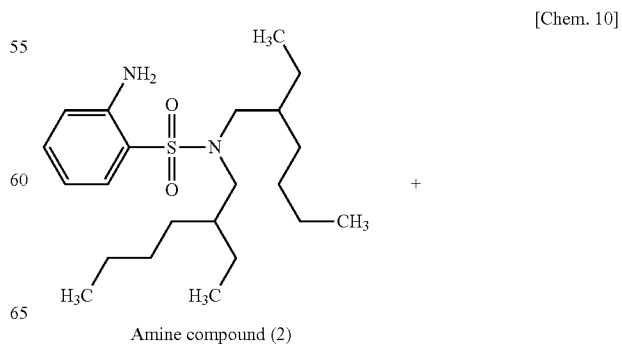

Amine compound (2)

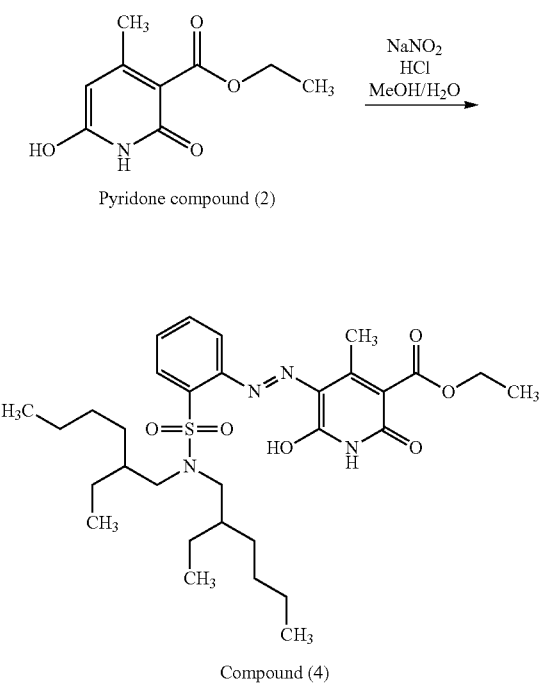

Pyridone compound (2)

Compound (4)

A solution of 3.00 g of amine compound (2) in 10 mL of methanol was cooled to 5° C., and 1.3 mL of 35% hydrochloric acid was dropwise added thereto. Furthermore, a solution of 0.58 g of sodium nitrite in 3 mL of water was dropwise added thereto, followed by stirring for 1 hour. Furthermore, 0.09 g of amidosulfuric acid was added thereto to decompose excess sodium nitrite to prepare diazotization solution B. Separately, a solution of 1.49 g of pyridone compound (2) in 10 mL of methanol was cooled to 5° C., and diazotization solution B was slowly dropwise added thereto while maintaining the temperature at 5° C. or less, followed by stirring at 0 to 5° C. for further 1 hour. After the completion of the reaction, a sodium carbonate aqueous solution was dropwise added to the reaction solution to neutralize the solution to pH 6. The precipitated solid was collected by filtration and was further washed with water. The resulting solid was purified by column chromatography (eluent: chloroform/methanol) and was recrystallized from a heptane solution to yield 3.0 g of Compound (4).

Analytical Results of Compound (4)

[1] $^1$H-NMR (400 MHz, CDCl$_3$, room temperature): δ (ppm)=0.74-0.87 (14H, m), 1.03-1.43 (21H, m), 2.32 (3H, s), 2.98-3.21 (4H, m), 7.23 (1H, t, J=7.63 Hz), 7.58 (1H, dd, J=7.63 Hz, 7.63 Hz), 7.84 (1H, d, J=7.63 Hz), 7.93 (1H, d, J=7.63 Hz), 8.14 (1H, br), 14.63 (1H, s).

[2] Mass spectrometry by MALDI-TOF-MS: m/z=603.451 (M-H)$^-$

Example 3

Production of Compound (23)

[Chem. 11]

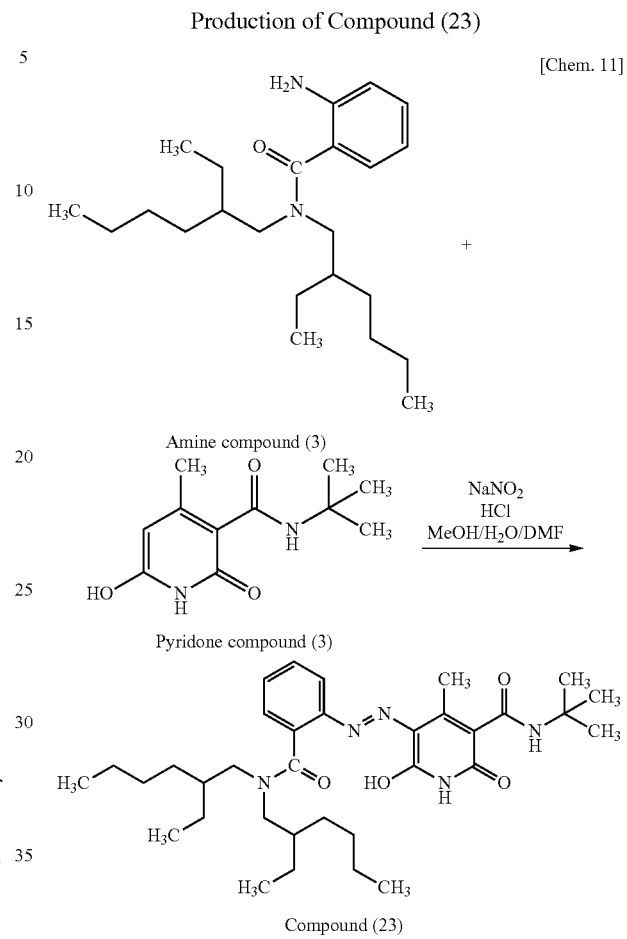

Amine compound (3)

Pyridone compound (3)

Compound (23)

A solution of 3.00 g of amine compound (3) in 20 mL of methanol was cooled to 5° C., and 1.5 mL of 35% hydrochloric acid was dropwise added thereto. Furthermore, a solution of 0.63 g of sodium nitrite in 3 mL of water was dropwise added thereto, followed by stirring for 1 hour. Furthermore, 0.10 g of amidosulfuric acid was added thereto to decompose excess sodium nitrite to prepare diazotization solution C. Separately, a solution of 1.87 g of pyridone compound (3) in 8 mL of dimethylformamide was cooled to 5° C., and diazotization solution C was slowly dropwise added thereto while maintaining the temperature at 5° C. or less, followed by stirring at 0 to 5° C. for further 3 hours. After the completion of the reaction, a sodium carbonate aqueous solution was dropwise added to the reaction solution to neutralize the solution to pH 6, and extraction with chloroform was performed. The chloroform layer was concentrated, and the resulting solid was purified by column chromatography (eluent: chloroform/methanol) and was recrystallized from a heptane/chloroform solution to yield 4.3 g of Compound (23).

Analytical Results of Compound (23)

[1] $^1$H-NMR (400 MHz, CDCl$_3$, room temperature): δ (ppm)=0.57-0.67 (3H, m), 0.69-0.79 (3H, m), 0.84-1.18 (14H, m), 1.27-1.48 (17H, m), 1.74-1.94 (2H, m), 2.55 (3H, s), 3.24 (2H, d, J=6.10 Hz), 3.35-3.69 (2H, m), 6.81 (1H, s), 7.20 (1H, dd, J=7.63 Hz, 7.63 Hz), 7.26 (1H, d, J=7.63 Hz), 7.47 (1H, dd, J=7.63 Hz, 7.63 Hz), 7.85 (1H, d, J=7.63 Hz), 8.21 (1H, br), 14.78 (1H, s).

[2] Mass spectrometry by MALDI-TOF-MS: m/z=594.530 (M-H)⁻

Example 4

Production of Compound (11)

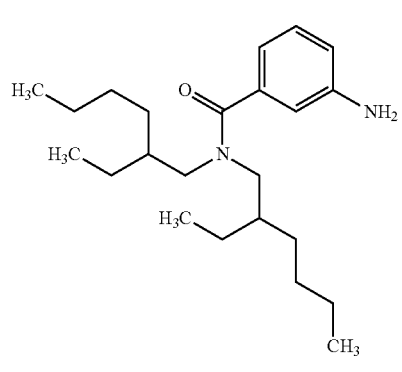

Amine compound (4)

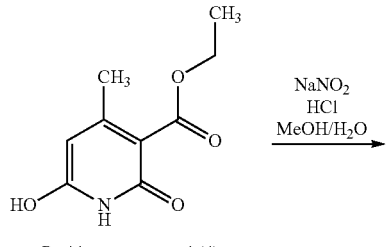

Pyridone compound (4)

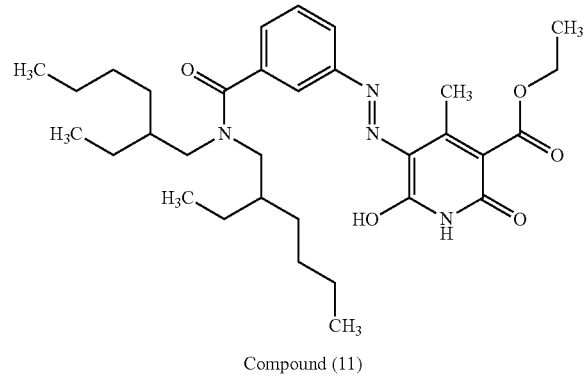

Compound (11)

Compound (11) was prepared as in Example 2 except that amine compound (4) and pyridone compound (4) were respectively used in place of amine compound (2) and pyridone compound (2) in Example 2.

Analytical Results of Compound (11)

[1] ¹H-NMR (400 MHz, CDCl₃, room temperature): δ (ppm)=0.72 (3H, t, J=7.25 Hz), 0.82 (3H, t, J=7.25 Hz), 0.89-0.99 (6H, m), 1.02-1.13 (4H, m), 1.15-1.26 (3H, m), 1.28-1.46 (12H, m), 1.74-1.88 (2H, m), 2.34 (3H, s), 3.18 (2H, d, J=6.87 Hz), 3.42-3.49 (2H, m), 4.40 (2H, q, J=7.12 Hz), 7.17-7.20 (1H, m), 7.40-7.49 (2H, m), 7.48 (1H, s), 8.87 (1H, br), 14.49 (1H, s).

[2] Mass spectrometry by MALDI-TOF-MS: m/z=567.708 (M-H)⁻

Example 5

Production of Compound (18)

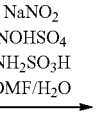

Amine compound (5)

Pyridone compound (5)

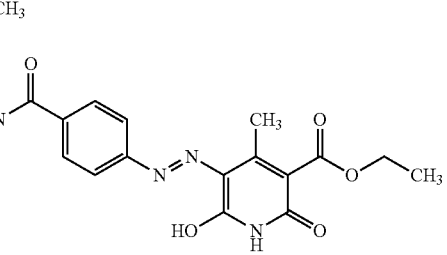

Compound (18)

Compound (18) was prepared as in Example 1 except that amine compound (5) and pyridone compound (5) were respectively used in place of amine compound (1) and pyridone compound (1) in Example 1.

Analytical results of Compound (18)

[1] ¹H-NMR (400 MHz, CDCl₃, room temperature): δ (ppm)=0.68-0.75 (3H, m), 0.81-0.87 (3H, m), 0.89-0.98 (6H, m), 1.02-1.12 (4H, m), 1.15-1.24 (3H, m), 1.29-1.46 (12H, m), 1.75-1.84 (2H, m), 2.37 (3H, s), 3.21 (2H, d, J=6.10 Hz), 3.44 (2H, d, J=5.34 Hz), 4.41 (2H, q, J=7.12 Hz), 7.45 (4H, s), 8.78 (1H, s), 14.49 (1H, s).

[2] Mass spectrometry by MALDI-TOF-MS: m/z=567.612 (M-H)⁻

Example 6

Production of Compound (26)

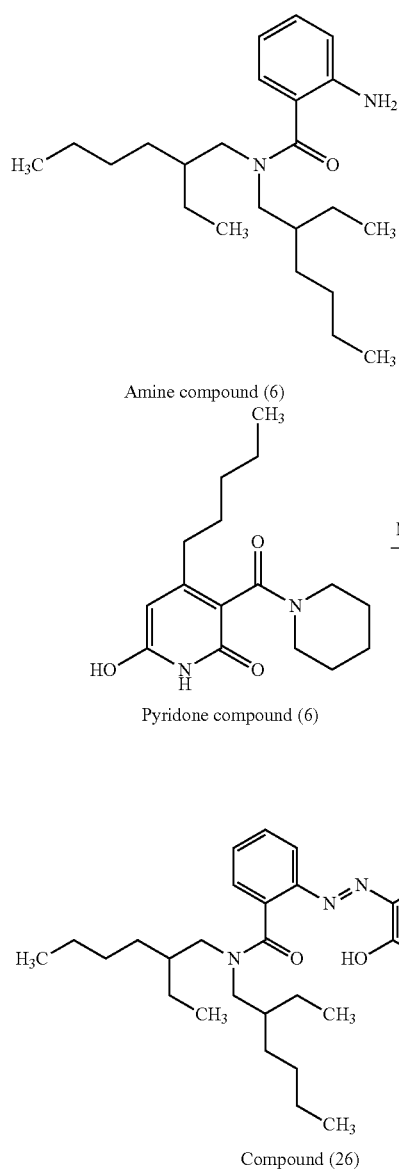

Compound (26)

Compound (26) was prepared as in Example 2 except that amine compound (6) and pyridone compound (6) were respectively used in place of amine compound (2) and pyridone compound (2) in Example 2.

Analytical Results of Compound (26)

[1] $^1$H-NMR (400 MHz, CDCl$_3$, room temperature): δ (ppm)=0.58-1.81 (47H, m), 2.66 (1H, br), 2.77 (1H, br), 3.22-3.36 (4H, m), 3.67-3.81 (2H, m), 7.18 (1H, t, J=7.25 Hz), 7.26 (1H, d, J=9.92 Hz), 7.45 (1H, t, J=7.63 Hz), 7.79 (1H, d, J=7.63 Hz), 8.10 (1H, s), 14.45 (1H, s).

[2] Mass spectrometry by MALDI-TOF-MS: m/z=662.464 (M-H)⁻

Example 7

Production of Compound (28)

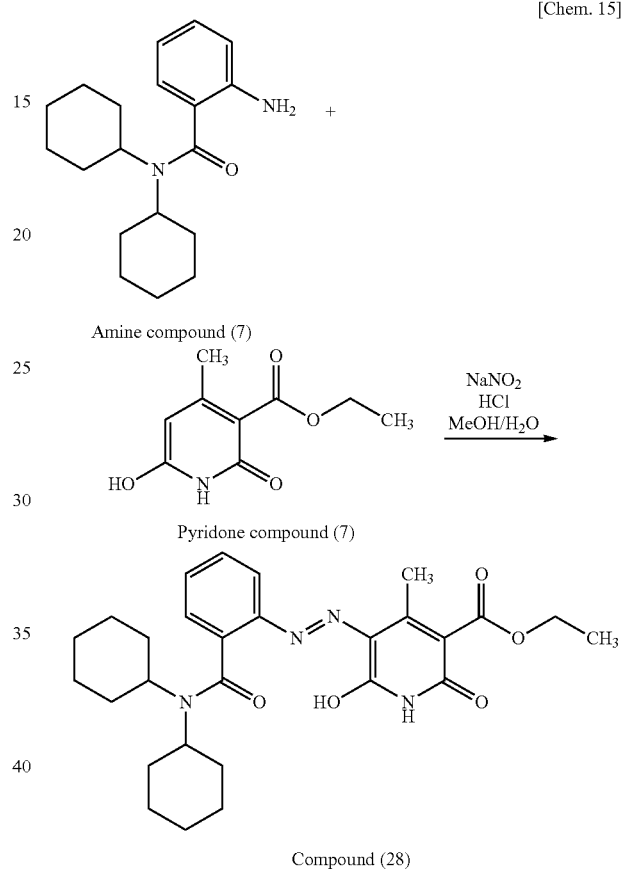

Compound (28)

Compound (28) was prepared as in Example 2 except that amine compound (7) and pyridone compound (7) were respectively used in place of amine compound (2) and pyridone compound (2) in Example 2.

Analytical Results of Compound (28)

[1] $^1$H-NMR (400 MHz, CDCl$_3$, room temperature): δ (ppm)=1.18-2.06 (20H, m), 2.37 (3H, s), 2.71 (1H, br), 3.23 (2H, br), 4.40 (2H, q, J=7.12 Hz), 7.19 (2H, d, J=6.10 Hz), 7.44 (2H, m), 7.75 (1H, d, J=11.06 Hz), 7.82 (1H, d, J=6.87 Hz), 8.08 (1H, s), 14.56 (1H, s).

[2] Mass spectrometry by MALDI-TOF-MS: m/z=507.261 (M-H)⁻

Production of Ink

Inks of the present invention and Comparative Inks were produced by the process described below.

Example 8

Production of Ink (1)

Ink (1) of the present invention was prepared by mixing 5 parts of Compound (1) as the water-insoluble coloring compound of the present invention, 350 parts of toluene, 350 parts of ethyl acetate, and 300 parts of 2-butanone.

Examples 9 to 14

Production of ink (4), (11), (18), (23), (26), and (28)

Inks (4), (11), (18), (23), (26), and (28) were prepared as in the production example of Example 8 except that Compounds (4), (11), (18), (23), (26), and (28) were respectively used in place of Compound (1) as the water-insoluble coloring compound in Example 8.

Comparative Examples 1 and 2

Production Examples of Comparative Inks (1) and (2)

Comparative Inks (1) and (2) were prepared as in the production example of Example 8 except that Comparative Compounds (1) and (2) shown below were respectively used in place of Compound (1) as the water-insoluble coloring compound in Example 8.

[Chem. 16]

Comparative Compound (1)

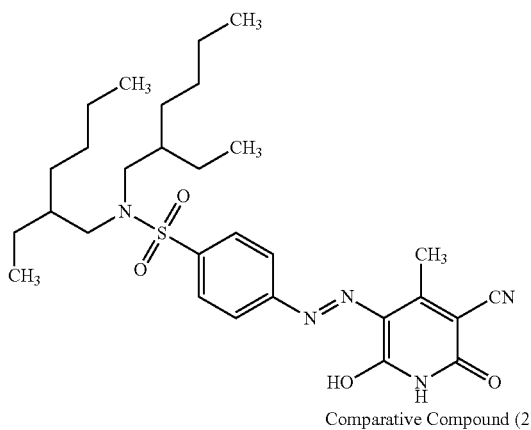

Comparative Compound (2)

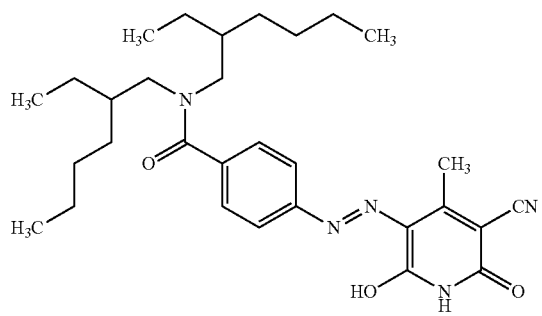

Evaluation

Evaluation of Solvent Solubility of Water-Insoluble Coloring Compound

The solvent solubilities of Compounds (1), (4), (11), (18), (23), (26), and (28) as the water-insoluble coloring compounds and Comparative Compounds (1) and (2) were evaluated by dissolving 30 mg of each compound in 0.7 mL of each solvent, toluene, methanol, ethyl acetate, or chloroform, at room temperature, and visually observing each solution according to the following evaluation criteria:

A: completely dissolved,

B: suspended material slightly remained, and

C: hardly dissolved.

Measurement of Saturation and Color Tone

Inks (1), (4), (11), (18), (23), (26), and (28) and Comparative Inks (1) and (2) were each applied onto paper for contrast ratio measurement by bar coating (Bar No. 10) and were air-dried overnight to produce image samples. Chromaticity values (L*, a*, b*) in the L*a*b* color system of each image sample were measured with a reflection densitometer SpectroLino (manufactured by Gretag Macbeth AG). The saturation (C*) was calculated based on the measured color characteristic values by the following expression:

$$C^* = \sqrt{(a^*)^2 + (b^*)^2}$$ [Math. 1]

Evaluation of Color Tone

It is recognized that a larger increase of the chromaticity in the green gamut at a constant value L* is useful for increasing the green gamut. In this Example, the color tone was evaluated based on the values of a* and b* at an L* of 92 as follows:

A: a* is less than −5.0 and b* is 100.0 or more,

B: a* is −5.0 or more and b* is 100.0 or more, and

C: b is less than 100.0.

In the above-described evaluation, criterion A indicates that the increase of the chromaticity in the green gamut is large, and criterion C indicates that the increase of the chromaticity in the green gamut is small.

Evaluation of Saturation

Saturation was evaluated based on the saturation C* at the time at which the image sample was produced by the bar coating (Bar No. 10). The saturation C* was calculated by the above-mentioned expression. The evaluation criteria are as follows:

A: 112.0<C*,

B: 108.0<C*≤112.0, and

C: C*<108.0.

The evaluation results of Examples and Comparative Examples are summarized in Table 1.

TABLE 1

| | | Solubility | | | | a*/b*/color tone | C* in bar coating (No. |
|---|---|---|---|---|---|---|---|
| | Compound | Toluene | Methanol | Ethyl acetate | Chloroform | evaluation at L* = 92 | 10)/Saturation evaluation |
| Example 8 | 1 | A | A | A | A | −11.3/110.1/A | 110.7/B |
| Example 9 | 4 | A | A | A | A | −10.3/112.8/A | 113.3/A |
| Example 10 | 11 | A | A | A | A | −11.3/109.8/A | 110.3/B |
| Example 11 | 18 | A | A | A | A | −8.2/117.4/A | 117.7/A |

TABLE 1-continued

|  | Compound | Solubility | | | | a*/b*/color tone evaluation at L* = 92 | C* in bar coating (No. 10)/Saturation evaluation |
|  |  | Toluene | Methanol | Ethyl acetate | Chloroform |  |  |
|---|---|---|---|---|---|---|---|
| Example 12 | 23 | A | A | A | A | −9.0/115.2/A | 115.5/A |
| Example 13 | 26 | A | A | A | A | −12.4/107.5/A | 108.2/B |
| Example 14 | 28 | A | A | A | A | −9.1/108.0/A | 108.4/B |
| Comparative Example 1 | Comparative Compound 1 | C | C | C | B | −2.6/105.4/B | 105.4/C |
| Comparative Example 2 | Comparative Compound 2 | C | C | C | B | −7.2/90.1/C | 90.4/C |

As obvious from Table 1, the water-insoluble coloring compounds of the present invention have higher solvent solubilities and better saturations and color tones compared to Comparative Compounds.

Production of Color Filter Resist Composition

Example 15

Ink (A) of the present invention was prepared by mixing 12 parts of Compound (1) as the water-insoluble coloring compound of the present invention and 120 parts of cyclohexanone and dispersing the mixture with an attritor (manufactured by Mitsui Mining Co., Ltd.) for 1 hour.

Color filter resist composition (1) of the present invention was prepared by slowly adding 22 parts of Ink (A) to a solution of 6.7 parts of an acrylic copolymer composition (weight average molecular weight Mw: 10000) composed of 40% by mass of n-butyl methacrylate, 30% by mass of acrylic acid, and 30% by mass of hydroxyethyl methacrylate in monomer ratios, 1.3 parts of dipentaerythritol pentaacrylate, and 0.4 parts of 2-benzyl-2-dimethylamino-1-(4-morpholinophenyl)-butanone (photopolymerization initiator) in 96 parts of cyclohexanone, stirring the mixture at room temperature for 3 hours, and filtering the reaction solution through a filter of 1.5 μm pore size.

Color filter (1) was produced by spin-coating color filter resist composition (1) on a glass substrate and then drying at 90° C. for 3 min, exposure of the entire surface to light, and post-curing at 180° C.

Examples 16 and 17

Color filter resist compositions (11) and (18) were prepared as in Example 15 except that Compounds (11) and (18) were respectively used in place of Compound (1) as the water-insoluble coloring compound in Example 15. Furthermore, color filters (11) and (18) were produced as in Example 15 except that the resulting color filter resist compositions (11) and (18) were respectively used in place of color filter resist composition (1).

Comparative Examples 3 and 4

Comparative color filter resist compositions (1) and (2) were prepared as in Example 15 except that Comparative Compounds (1) and (2) were respectively used in place of Compound (1) as the water-insoluble coloring compound in Example 15. Furthermore, comparative color filters (1) and (2) were produced as in Example 15 except that the resulting comparative color filter resist compositions (1) and (2) were respectively used in place of color filter resist composition (1).

Evaluation

Color filters (1), (11), and (18) prepared in Examples 15 to 17 were visually investigated and were confirmed to have good color tones. The results demonstrate that the coloring materials, Compounds (1), (11), and (18), have high solvent solubilities and thereby can be uniformly spin-coated on the glass substrate.

Comparative color filters (1) and (2) prepared in Comparative Examples 3 and 4 were visually investigated and were confirmed to show ununiform color tones. The results demonstrate that the coloring materials, Comparative Compounds (1) and (2), have poor solvent solubilities and thereby cannot be uniformly spin-coated on the glass substrate.

Preparation of Thermal Transfer Recording Sheet

Example 18

Ink (B) of the present invention was prepared by gradually adding 5 parts of a polyvinyl butyral resin (Denka 3000-K, manufactured by Denki Kagaku Kogyo K.K.) to a solution of 13.5 parts of Compound (1) as the water-insoluble coloring compound of the present invention in a mixture of 45 parts of methyl ethyl ketone and 45 parts of toluene with stirring.

Ink (B) was applied onto a polyethylene terephthalate film (Lumirror, manufactured by Toray Industries, Inc.) having a thickness of 4.5 μm so as to have a dried thickness of 1 μm and was dried to produce thermal transfer recording sheet (1).

Examples 19 and 20

Thermal transfer recording sheets (4) and (23) were produced as in Example 18 except that Compounds (4) and (23) were respectively used in place of Compound (1) as the water-insoluble coloring compound in the production example of Example 18.

Comparative Examples 5 and 6

Comparative thermal transfer recording sheets (1) and (2) were produced as in Example 18 except that Comparative Compounds (1) and (2) were respectively used in place of Compound (1) as the water-insoluble coloring compound in Example 18.

Evaluation

Thermal transfer recording sheets (1), (4), and (23) prepared in Examples 18 to 20 were visually confirmed not to have color unevenness. Furthermore, recorded matters formed using these thermal transfer recording sheets showed good saturations and good color tones.

Comparative thermal transfer recording sheets (1) and (2) prepared in Comparative Examples 5 and 6 were visually confirmed to have color unevenness. Furthermore, recorded matters formed using these thermal transfer recording sheets had color unevenness.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-010326, filed Jan. 20, 2012, which is hereby incorporated by reference herein in its entirety.

The invention claimed is:

1. A water-insoluble coloring compound having a structure represented by Formula (1):

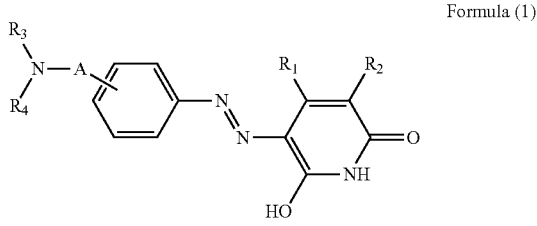

Formula (1)

in Formula (1), $R_1$ represents an alkyl group, an aryl group, or an amino group; $R_2$ represents a carboxylic acid ester, a carboxylic acid monoalkylamide or a carboxylic acid dialkylamide; A represents a carbonyl group or a sulfonyl group; and $R_3$ and $R_4$ each independently represent an n-butyl group, an octyl group, a cyclohexyl group, a 2-ethylhexyl group, a dodecyl group or a phenyl group.

2. The water-insoluble coloring compound according to claim 1, wherein in Formula (1), $R_3$ and $R_4$ are the same functional group.

3. The water-insoluble coloring compound according to claim 1, wherein in Formula (1), $R_2$ is a carboxylic acid ester.

4. An ink comprising the water-insoluble coloring compound according to 1.

5. A thermal transfer recording sheet comprising
a base material and
a coloring material layer formed on the base material from a composition containing the water-insoluble coloring compound according to claim 1.

6. A color filter resist composition comprising the water-insoluble coloring compound according to claim 1.

7. The water-insoluble coloring compound according to claim 1, wherein in Formula (1), $R_3$ and $R_4$ each independently represent a n-butyl group or a 2-ethylhexyl group.

8. The water-insoluble coloring compound according to claim 1, wherein in Formula (1), both $R_3$ and $R_4$ represent a 2-ethylhexyl group.

* * * * *